United States Patent [19]

Fuchigami et al.

[11] 3,948,807

[45] Apr. 6, 1976

[54] OXIDE CATALYSTS AND PROCESS FOR PREPARATION THEREOF

[75] Inventors: Yoshio Fuchigami, Kurashiki; Yusaku Arima, Kitakyushu, both of Japan

[73] Assignee: Kuraray Co., Ltd., Japan

[22] Filed: Jan. 2, 1974

[21] Appl. No.: 429,705

[30] Foreign Application Priority Data

Feb. 9, 1973 Japan................................ 48-16870
Jan. 13, 1973 Japan................................ 48-6937

[52] U.S. Cl................................ 252/456; 252/461
[51] Int. Cl.²...................... B01J 29/16; B01J 29/26
[58] Field of Search............................ 252/456, 461

[56] References Cited
UNITED STATES PATENTS

| | | | |
|---|---|---|---|
| 3,055,842 | 9/1962 | Robinson............................ | 252/461 |
| 3,464,930 | 9/1969 | Friedrichsen et al........... | 252/461 X |
| 3,496,233 | 2/1970 | Bohemen et al................ | 252/456 X |
| 3,562,185 | 2/1971 | Friedrichsen et al............. | 252/456 |
| 3,799,886 | 3/1974 | Felice et al........................ | 252/461 |
| 3,799,888 | 3/1974 | Suvorov et al................... | 252/461 X |

*Primary Examiner*—Paul F. Shaver
*Attorney, Agent, or Firm*—Sherman & Shalloway

[57] ABSTRACT

An improved process for preparing an oxide catalyst comprising vanadium oxide and titanium oxide and silica as an optional component, in which more than 50% of the titanium oxide is in the rutile crystalline form, which comprises calcining a mixture of a vanadium compound and amorphous hydrogel of titanium oxide or a mixture further containing silica, in an oxidizing atmosphere at a temperature of 400° to 600°C.; and a catalyst so obtained. This oxide catalyst is very suitable as a fluidized bed catalyst for prepaing acetic acid by gaseous phase oxidation of butenes.

9 Claims, No Drawings

OXIDE CATALYSTS AND PROCESS FOR PREPARATION THEREOF

This invention relates to an oxide catalyst composed of vanadium oxide and titanium oxide or an oxide catalyst composed of vanadium oxide, titanium oxide and silica in which more than 50% of the titanium oxide is in the rutile crystalline form; and an improved process for preparing this catalyst. This catalyst is used for oxidizing hydrocarbons, and is especially useful as a catalyst for preparing acetic acid by the gaseous phase oxidation of butenes.

It is known from U.S. Pat. No. 3,431,297 and German Patent No. 1,279,011 that a catalyst composed of vanadium oxide and titanium oxide is used for preparing acetic acid by the gas phase oxidation of butenes. According to the disclosures of these patent specifications, this catalyst is prepared by neutralizing an acidic homogeneous mixed solution containing a vanadium compound and a titanium compound to form a co-precipitate, drying the co-precipitate at 50° to 200°C., and then calcining it at 300° to 700°C. The titanium oxide component in the catalyst so prepared consists essentially of anatase-type titanium oxide.

After the issuance of these patents, investigations, in which one of the co-inventors of the present application was involved, led to the development of a catalyst composed of vanadium oxide and titanium oxide in which at least 50% of the titanium oxide component is in the rutile crystalline form, and to the discovery that this catalyst exhibits better catalytic efficiency than a catalyst of the same composition in which a greater part of the titanium oxide component is in the anatase crystalline form. This is disclosed in DAS No. 2,026,744, French Patent No. 2,056,232 and U.S. patent application Ser. No. 39507 filed May 21, 1970. These patent specifications describe one method for preparing such a catalyst, which comprises neutralizing an acidic homogeneous mixed solution containing a vanadium compound and a titanium compound to cause co-precipitation, and calcining the resulting precipitate at 450° to 600°C. in an atmosphere of a low oxygen partial pressure, that is, an atmosphere in which the concentration of oxygen is restricted to not more than 10%. If the concentration of oxygen in the atmosphere is above 10%, the desired catalyst in which at least 50% of the titanium oxide component is in the rutile crystalline form cannot be obtained. Thus, the catalyst preparation method disclosed in these patent specifications includes a calcination step which requires an atmosphere having a specific low concentration of oxygen. However, it is very difficult to maintain the oxygen concentration in a calcination furnace, especially a continuous calcination furnace, at a low level, and commercial performance of this method is almost impossible. Accordingly, there has been a demand for the development of a method of preparing such a catalyst on a commercial scale without any restriction on the oxygen concentration of the atmosphere in which the calcination is carried out.

One object of this invention is to provide an improved process for easily preparing a vanadium oxide-titanium oxide catalyst in which more than 50% of the titanium oxide is in the rutile crystalline form, the process meeting the above-mentioned demand.

Another object of this invention is to provide a vanadium oxide-titanium oxide-silica catalyst in which more than 50% of the titanium oxide is in the rutile crystalline form, and which is very superior as a catalyst for producing acetic acid by the gaseous phase oxidation of butenes.

According to this invention, there is provided an improved process for preparing an oxide catalyst composed of vanadium oxide and titanium oxide in which more than 50% of the titanium oxide is in the rutile crystalline form, which comprises calcining an intimate mixture of a vanadium compound and a titanium oxide hydrogel which when dried at 250°C. will give titanium oxide having a crystallite size of not more than 70 A as calculated by the Sherrer method based on its X-ray diffraction peak at $2\theta=25.4°$ (anatase), in an oxidizing atmosphere at a temperature of 400° to 600°C.

According to this improved process, calcination can be performed without any influence by the oxygen concentration of the calcination atmosphere, and most conveniently it can be carried out in an atmosphere of air, to produce the desired catalyst easily.

The titanium oxide hydrogel used in the present invention is a hydrogel capable of giving titanium oxide whose crystallite size is not more than 70 A upon drying at 250°C. In practice, sizes of less than about 20 A cannot be measured by means of X-rays, and titanium oxides having such a size are considered as completely amorphous. Inclusive of such completely amorphous form, titanium oxide having a size of not more than 70 A could be regarded as substantially amorphous. For brevity, such a titanium oxide will be referred to in the following description as amorphous titanium oxide.

It has been found that the titanium oxide hydrogel which gives amorphous titanium oxide when dried at 250°C. can be easily prepared. One preferred method will be described below. An aqueous solution of a water-soluble titanium salt such as titanium sulfate, titanium nitrate or titanium tetrachloride is neutralized with a basic substance such as ammonia or an alkali hydroxide at a temperature of not more than 70°C., preferably not more than 45°C. until the pH of the solution reaches 4–10, preferably 7–9 to form a precipitate of fine titanium oxide hydrogel. When the temperature and pH conditions fall outside the above-specified ranges, the desired hydrogel is difficult to prepare. In order to form fine precipitates, the pH value after neutralization is desirably high, and the operating temperature is desirably low. The formation of fine precipitates is also affected to some extent by the concentrations of the titanium salt solution and the basic solution, the sequence of mixing the two solutions, and the neutralization time. Higher concentrations of these solutions are preferred. As regards the order of mixing, the basic solution may be added to the titanium solution, or vice versa. However, most preferably, the two solutions are poured simultaneously and mixed. The neutralization time is preferably as short as possible, but usually, it is about 10 to 30 minutes. These conditions may be in accordance with the general techniques in the conventional art of forming fine precipitates. The basic substance for neutralization is preferably ammonia which is volatile, because of the ease of removing an excessive portion afterwards. If titanium tetrachloride is used as the titanium salt and ammonia, as a neutralizing reagent, ammonium chloride is formed, and a fume of residual ammonium chloride is evolved at the time of calcination for catalyst preparation and renders the operation somewhat inconvenient. This inconvenience can be avoided if titanium sulfate is used as the titanium salt. It is preferred that the precipitate of titanium oxide hydrogel formed by the neutralization of an aqueous solution of the titanium salt should be washed with water. The resulting precipitate is mixed intimately with a vanadium compound.

The vanadium compound may be an oxide or a salt. The intimate mixture of the vanadium compound and the titanium oxide hydrogel is preferably prepared by mixing an aqueous solution of the vanadium compound with the titanium oxide hydrogel to form a slurry, and the slurry is dried. The aqueous solution of the vanadium compound can be obtained by dissolving the vanadium compound in an aqueous solution of a reducing organic acid such as oxalic acid, maleic acid, tartaric acid, or citric acid. The use of oxalic acid which is low in cost and easily available is advantageous. In this case, an aqueous solution of vanadyl oxalate is obtained.

The atomic ratio of titanium to vanadium in the final oxide catalyst obtained is determined by the mixing ratio of the titanium oxide hydrogel to the vanadium compound. This atomic ratio is from 0.1 to 10. If the proportion of the titanium component is too large, the activity of the resulting catalyst tends to decrease, and if the proportion of the vanadium component is too large, there is a tendency towards excessive oxidation reaction in a particular reaction to which the catalyst is applied. The preferred atomic ratio is 0.3 to 3, and the most preferred ratio is 0.4–1.

The mixing of the titanium oxide hydrogel with the aqueous solution of the vanadium compound is performed by stirring. In order to ensure more uniform and intimate mixing of the two, a customary means such as a homogenizer or colloid mill may be used. At the time of mixing, other components may be added simultaneously. Desirably, the concentration of the solid component in the mixed slurry is moderately large in view of the subsequent drying step.

The method of drying the mixed slurry is properly chosen according to whether the intended catalyst is a fixed bed catalyst or fluidized bed catalyst. In the case of the former, any desired method of drying can be employed, whereas in the case of the latter, a spray drying method is desirable.

When the mixed composition dried is calcined at a temperature of 400° to 600°C. in an oxidizing atmosphere, the intended catalyst containing vanadium (V) oxide and titanium oxide can be obtained. It is not at all necessary to increase or decrease the oxygen concentration of the oxidizing atmosphere to a specified value, but calcination can be performed in an atmosphere of air. The calcination may be carried out by the use of any type of calcination furnaces. For commercial performance, it is advantageous that calcination is carried out continuously under a stream of air using a rotary kiln adapted to be heated exteriorly.

It is surprising that when an intimate mixture of the titanium oxide hydrogel capable of giving amorphous titanium oxide when dried at 250°C. is calcined at a temperature of 400° to 600°C., more than 50% of the titanium oxide component in the resulting composition is converted to the rutile crystalline form. It was previously generally believed that titanium oxide per se cannot be changed to a rutile crystalline form unless heated to a temperature higher than about 900°C.

The oxide catalyst obtained by the process of this invention is especially suitable as a catalyst to be used for the preparation of acetic acid by the gaseous phase oxidation of butenes. Since this gaseous phase oxidation reaction generates heat in an amount of as much as 280 Kcal/mol (butene), the reaction system is most suitably based on a fluidized catalyst bed. The application of the fluidized bed serves to render the temperature within the reaction system uniform, and give rise to a high selectivity to the formation of acetic acid. In addition, a feed gas having a high butene concentration within the explosive limit can be supplied unlike a fixed bed type reaction system to which such a feed gas cannot be used. Thus, a high productivity of acetic acid can be realized.

The explosive limit concentration of butene in air is about 1.7 to 9%. The catalyst of this invention containing a rutile-rich titanium oxide affords a higher selectivity to the formation of acetic acid than the catalyst containing anatase titanium oxide which is disclosed in the U.S. Pat. No. 3,431,297 and German Patent No. 1,279,011, and the higher the concentration of butene in the feed gas, the more remarkable is the difference in selectivity between these two catalysts.

It has been found that a catalyst containing a silica component in addition to the vanadium oxide and titanium oxide described above is very superior as a fluidized bed catalyst for the gaseous phase oxidation of butene. The preparation and the properties of such a catalyst will be described in detail below. The silica component is most preferably in the form of colloidal silica sol, and can be added simultaneously with the admixing of the amorphous titanium oxide hydrogel and an aqueous solution of the vanadium compound. The silica concentration of the silica sol is preferably high, for example, 15 to 50%, in order to enhance the efficiency of the subsequent drying step. The amount of the silica to be added is 10 to 90% by weight based on the final catalyst composition. The mixed slurry consisting of the titanium oxide hydrogel, the aqueous solution of the vanadium compound and silica sol is then spray dried. The spray drying is preferably performed by using a slurry having a high solids content, for example, 20 to 30% by weight calculated as a total amount of oxides dried, and rendering the hot air temperature as low as possible, for example adjusting it to 70° to 150°C. The dried composition is then calcined at 400° to 600° C. in an oxidizing atmosphere to form the desired catalyst.

The addition of the silica component imparts attrition resistance to the catalyst which can endure use for prolonged periods of time as a fluidized bed catalyst, and there can be realized a catalyst having a size distribution suitable for good and stable fluidization. The particle size distribution suitable for stability of fluidization is such that the catalyst contains 5 to 30% of particles having a size of not more than 44 microns, and not more than 20% of particles having a particle size of not less than 149 microns, and has an average particle size of 50 to 90 microns.

Furthermore, the addition of the silica component contributes to the improvement of the catalyst properties by controlling the specific surface area, the pore volume and the pore radius of the catalyst. A catalyst obtained in the absence of silica has a pore distribution over a wide range of 50 A to 100,000 A, but when silica is added in an amount of 50% based on the total weight of the catalyst, a catalyst having a narrow pore distribution of 50 A to 2000 A is obtained. It appears that such a narrow and sharp pore distribution contributes to the good properties of the catalyst.

The fluidized bed catalyst of this invention containing a silica component has the following characteristics.

| | |
|---|---|
| Titanium/vanadium atomic ratio | 0.1 – 10 |
| Proportion of the rutile form in the titanium oxide component[1] | more than 50% |
| Silica content | 10–90% by weight |
| Bulk density[2] | 0.6 – 1.2 g/ml. |
| Specific surface area[3] | 10 – 200 m²/g |
| Pore volume[4] | 0.1 – 0.5 ml/g |
| Pore radius[5] | more than 50 A |

Note

[1] The rutile content is measured by the X-ray powder diffraction method, i.e., the X-ray (Cu, Ka ray) diffraction of the pulverized catalyst and calculated by the following equation, wherein IA is the diffraction at $2\theta=25.4°$ referring to anatase, and IR is the diffraction at $2\theta=27.5°$ referring to rutile.

Rutile content (%) = $\frac{IR}{IR + IA} \times 100$

[2] Bulk density
Loose packing densities by a measuring cylinder method.

[3] Specific surface area
By the B.E.T. method, the surface area is calculated from the amount of nitrogen adsorbed to a single molecule layer.

[4] Pore volume
By the B.E.T. method, the volume of pores having a pore radius of not more than 600 A is calculated from the amount of nitrogen condensed at a pressure of 735 mmHg.

[5] Pore radius
By the mercury introducing method, the pore radius corresponding to 50% of the total volume of all pores which have a maximum pressure of 60,000 lb/cm² as measured by a porosimeter.

The following Examples illustrate the present invention. The properties of the catalyst were measured by the above methods. The particle size was measured by the micromesh sieve method, and the attrition resistance was measured by the A.C.C. method which is described in "Test Methods for Synthetic Fluid Cracking Catalyst", (American Cyanamid Co.), W. L. Jr. Forsythe and W. R. Hertwig, Ind. Eng. Chem., 41, 1200 (1949).

EXAMPLE 1

418 g of pure water was added to 1082 g of titanium sulfate (TiO₂ 13.84%, H₂SO₄ 6.43%) to form 1500 g of a 10% aqueous solution of titanium sulfate. With thorough stirring, 1700 g of 15% aqueous ammonia was added to the resulting solution in the course of 10 minutes. During this time, the vessel used was cooled with flowing water, so as to maintain the temperature of the liquid at not more than 40°C. The pH of titanium sulfate and aqueous ammonia after neutralization was 8.12. The resulting hydrogel of titanium oxide was filtered, and this precipitate was put into 3 times the weight of the mother liquor of pure water, and the mixture was thoroughly stirred and allowed to stand. The supernatant liquid was discarded. This decantation operation was repeated 3 times, and ammonium sulfate was removed from the precipitate. After washing, a small amount of the precipitate was dired for 3 hours at 110°C. and subsequently for 18 hours at 250°C. The titanium oxide obtained was found by the X-ray diffraction method to be amorphous.

199 g of vanadium pentoxide was suspended in 398 g of pure water, and heated with stirring. When the temperature of the liquid exceeded 80°C., 418 g of oxalic acid was gradually added to reduce vanadium and form a vanadyl oxalate solution. When all the oxalic acid was added, the complete reaction of vanadium to form a homogeneous solution was confirmed, followed by cooling to 40°C. The hydrogel of titanium oxide after washing was added with thorough stirring to the resulting vanadyl oxalate solution, and the mixture was spray dried by a spray dryer. The fine spherical particles so spray dried were calcined in a muffle furnance at 250°C. for 3 hours. The resulting catalyst was composed of titanium oxide and vanadium oxide with a Ti/V atomic ratio of 0.86. The rutile content of the titanium oxide component was 98%.

EXAMPLE 2

7.54 Kg of a 10% aqueous solution of titanium sulfate was placed in a vessel and with thorough stirring 7.80 Kg of 15% aqueous ammonia was added. The time required for the addition was 14 minutes, and the slurry after the addition had a temperature of 40.6°C. and a pH of 8.3. The resulting gel of titanium hydroxide was separated by filtration and dehydrated, and re-suspended in 3 times the amount of the mother liquor of pure water, followed by allowing it to settle. The supernatant liquid was discarded. This decantation operation was repeated three times, and ammonium sulfate as a byproduct was removed. A small of the precipitate was dried for 18 hours at 250°C and the titanium oxide obtained was found to be amorphous.

On the other hand, 998 g of vanadium pentoxide was suspended in 1996 g of pure water, and heated with stirring. When the temperature exceeded 80°C., 2096 g of oxalic acid was gradually added to reduce vanadium and form a solution of vanadyl oxalate.

The titanium hydroxide gel was well mixed with the vanadyl oxalate solution, and 5.84 Kg of aqueous colloidal solution containing 30% silica. The total amount of titanium dioxide, vanadium pentoxide and silica present in the resulting slurry was 24.0% based on the weight of the slurry.

The slurry was passed twice through a homogenizer to render it homogeneous, and then spray dried to form fine spherical particles. The spray drying was carried out by using a rotary disc-type spray dryer of the concurrent type. The temperature of the hot air was 113° to 130°C. at the inlet and 90° to 95°C. at the outlet. The resulting particles had a water content of 31.4%. Microscopic observation of the particles showed hardly any hollow particles, and also showed that the particles are nearly spherical in shape. The dried particles were calcined at 520°C. for 3 hours using a box-shaped muffle furnance. The catalyst obtained had the following characteristics.

| | |
|---|---|
| Ti/V atomic ratio | 0.86 |
| Rutile content of the titanium oxide | 96.3 % |
| SiO₂ content | 50 % |
| Bulk density | 0.90 g/ml. |
| Specific surface area | 42 m²/g |
| Pore volume | 0.16 ml/g |
| Pore radius | 250 A |
| Particle size | 58 μ on an average |
| Attrition resistance | 3.0 % |

EXAMPLE 3

1700 g of 15% aqueous ammonia was placed in a vessel, and with stirring a 10% aqueous solution of titanium solution was added in the course of 10 minutes. The pH of the solution after neutralization was 8.0 and its temperature was 39.2°C. The resulting precipitate was washed in the same way as in Example 1. A small amount of the precipitate was dried at 110°C. for 3 hours, and at 250°C. for 18 hours. The crystalline form of the titanium oxide obtained was found to be amorphous.

The precipitate of titanium hydroxide after this washing procedure was mixed with a vanadyl oxalate solution containing 243 g of vanadium as vanadium pentoxide, and then 1420 g of 30% colloidal silica was added, and dispersed well. The mixture was spray dried to form fine spherical particles. The particles obtained were then calcined at 520°C. for 3 hours in a muffle furnace. The resulting catalyst was composed of the oxides of titanium, vanadium, and silicon which contained 50% by weight of a silica component and had a Ti/V atomic ratio of 0.86. The titanium oxide crystals had a rutile content of 80%.

COMPARATIVE EXAMPLE 1

361 g of titanium sulfate (the same as that used in Example 1) was diluted with water to form 1000 g of a 5% aqueous solution of titanium sulfate. The diluted titanium sulfate solution was heated at 105°C. for 2 hours without adding ammonia to hydrolyze the titanium sulfate and to obtain a precipitate of titanium hydroxide. The precipitate was filtered, and washed three times with 3 times the amount of the mother liquor of pure water by the decantation method. After washing, a small amount of the precipitate was dried at 110°C. for 3 hours, and at 250°C. for 18 hours. The crystallite size of the titanium oxide obtained was 90 A as calculated by the Sherrer method, and it was confirmed that the titanium oxide was crystallized.

The precipitate after washing was mixed with a vanadyl oxide solution containing 66 g of vanadium as vanadium pentoxide, and further 387 g of 30% colloidal silica was mixed. The mixture was spray dried to form fine spherical particles. The particles obtained were calcined at 520°C. for 3 hours in a muffle furnace. The resulting catalyst had a Ti/V atomic ratio of 0.86, and a silica content of 50% by weight, and the titanium oxide had a rutile content of 27%.

COMPARATIVE EXAMPLE 2

500 g of a 10% aqueous solution of titanium sulfate was placed in a vessel, and with thorough stirring, 1.5% aqueous ammonia was added in an amount of 488 g in the course of 10 minutes. The solution after neutralization had a temperature of 39.2°C. and a pH of 4.3. Ammonium sulfate was removed from the resulting precipitate in the same way as in Example 1, and a small amount of the residue was dried at 110°C. for 3 hours and at 250°C. for 18 hours. The resulting titanium oxide had a crystallite size of 120 A measured by the Sherrer method. It was confirmed that the titanium oxide was crystallized.

The precipitate of titanium hydroxide after washing was mixed with a vanadyl oxalate solution containing vanadium in an amount of 66 g as vanadium pentoxide, and 387 g of 30% colloidal silica was further added. The mixture was spray dried to form fine spherical particles. The particles were calcined at 520°C. for 3 hours in a muffle furnace for 3 hours. The resulting catalyst had a Ti/V atomic ratio of 0.86 and a silica content of 50% by weight. The titanium oxide had a rutile content of 0%.

REFERENTIAL EXAMPLE

Example of Oxidation Reaction:

Butene-1 was oxidized using each of the catalysts obtained in Examples 1 to 3, and Comparative Examples 1 and 2. 100 ml. of each of the catalysts was placed into a Pyrex glass fluidized bed reactor having an inside diameter of 38 mm, and a starting gas consisting of 67 Nl/hr of air and 3.4 Nl/hr of butene-1 was passed through the reactor, and the resulting gaseous produce was passed through a condenser, to separate the resulting water and acetic acid. The results are shown in Table 1.

Table 1

| Catalyst used | Rutile content (%) of $TiO_2$ | Reaction temperature (°C) | Conversion of butene (mol%) | Yield of acetic acid (mol%) |
|---|---|---|---|---|
| Example 1 | 98 | 256 | 94.0 | 60.0 |
| Example 2 | 96.3 | 276 | 93.8 | 61.6 |
| Example 3 | 80 | 272 | 92.0 | 58.0 |
| Comparative Example 1 | 27 | 250 | 94.1 | 32.0 |
|  |  | 240 | 84.0 | 45.5 |
| Comparative Example 2 | 0 | 234 | 85.0 | 43.0 |

What we claim is:

1. In a process for preparing an oxide catalyst composed of vanadium oxide and titanium oxide in which more than 50% of the titanium oxide is in the rutile crystalline form, the improvement comprising calcining an intimate mixture of (a) vanadium oxide or a vanadium compound which, when calcined in an oxidizing atmosphere at 400° to 600°C. will give vanadium oxide and (b) a titanium oxide hydrogel which when dried at 250°C. will give titanium oxide having a crystallite size of not more than 70 A as calculated by the Sherrer method based on its X-ray diffraction peak at $2\theta=25.4°$, in an oxidizing atmosphere containing more than 10% by volume of oxygen at a temperature of 400° to 600°C.

2. In a process for preparing an oxide catalyst composed of vanadium oxide, titanium oxide and silica in which more than 50% of the titanium oxide is in the rutile crystalline form, the improvement comprising calcining an intimate mixture of (a) vanadium oxide or a vanadium compound which, when calcined in an oxidizing atmosphere at 400° to 600°C will give vanadium oxide, (b) a titanium oxide hydrogel which when dried at 250°C. will give titanium oxide having a crystallite size of not more than 70 A as calculated by the Sherrer method based on its X-ray diffraction peak at $2\theta=25.4°$, and (c) silica, in an oxidizing atmosphere containing more than 10% by volume of oxygen at a temperature of 400° to 600°C.

3. The process of claim 1 in which the intimate mixture is prepared by drying a mixture consisting of an aqueous solution of the vanadium oxide or vanadium compound and the hydrogel of titanium oxide.

4. The process of claim 2 wherein said intimate mixture is prepared by drying a mixture consisting of an aqueous solution of the vanadium oxide or vanadium compound, the hydrogel of titanium oxide and a aqueous colloidal solution of silica.

5. The process of claim 4 wherein said intimate mixture consists of components in such a proportion that the final catalyst composition to be obtained by calcination has a titanium-to-vanadium atomic ratio of 0.1 to 10 and a silica content of 10 to 90% by weight.

6. The process of claim 4 wherein said drying is spray drying.

7. An oxide catalyst suitable for use as a fluidized bed catalyst for preparing acetic acid by the gaseous phase oxidation of butenes, said catalyst consisting essentially of vanadium oxide, titanium oxide and silica, and having the following features:

| | |
|---|---|
| a titanium-to-vanadium atomic ratio | 0.1 to 10 |
| a rutile content of titanium oxide | more than 50% |
| a silica content based on the total weight of the composition | 10–90% by weight |
| a bulk density | 0.6 – 1.2 g/ml. |
| a specific surface area | 10 – 200 m$^2$/g |
| a pore volume | 0.1 – 0.5 ml/g |
| a pore diameter | at least 50 A. |

8. The process of claim 1 wherein said oxidizing atmosphere is air in which the calcination is conducted.

9. The process of claim 1 wherein said intimate mixture consists of components (a) and (b) in such a proportion that the final catalyst composition to be obtained by calcination has a titanium-to-vanadium atomic ratio of from 0.1 to 10.

* * * * *

UNITED STATES PATENT OFFICE
CERTIFICATE OF CORRECTION

Patent No. 3,948,807　　　　　　　　　Dated April 6, 1976

Inventor(s) Yoshio Fuchigami et al.

It is certified that error appears in the above-identified patent and that said Letters Patent are hereby corrected as shown below:

Item 73, line 1, before "Japan" insert -- Kurashiki, --.

Signed and Sealed this

Fourteenth Day of December 1976

[SEAL]

*Attest:*

RUTH C. MASON
*Attesting Officer*

C. MARSHALL DANN
*Commissioner of Patents and Trademarks*